(12) United States Patent
Holmqvist

(10) Patent No.: US 9,033,932 B2
(45) Date of Patent: May 19, 2015

(54) MEDICAMENT DELIVERY DEVICE

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 448 days.

(21) Appl. No.: 13/698,655

(22) PCT Filed: May 9, 2011

(86) PCT No.: PCT/SE2011/005081
§ 371 (c)(1),
(2), (4) Date: Dec. 3, 2012

(87) PCT Pub. No.: WO2011/145999
PCT Pub. Date: Nov. 24, 2011

(65) Prior Publication Data
US 2013/0116625 A1    May 9, 2013

Related U.S. Application Data

(60) Provisional application No. 61/346,679, filed on May 20, 2010.

(30) Foreign Application Priority Data

May 20, 2010 (SE) ...................................... 1050500

(51) Int. Cl.
*A61M 5/00*        (2006.01)
(Continued)

(52) U.S. Cl.
CPC .......... *A61M 5/31578* (2013.01); *A61M 5/2033* (2013.01); *A61M 5/24* (2013.01); *A61M 5/3202* (2013.01); *A61M 2005/2073* (2013.01)

(58) Field of Classification Search
CPC .......... A61M 2005/2073; A61M 5/24; A61M 5/31578; A61M 5/3202
USPC ......................................................... 604/187
See application file for complete search history.

(56) References Cited

FOREIGN PATENT DOCUMENTS

| GB | 2451664 A | 2/2009 |
|---|---|---|
| GB | 2467637 A | 8/2010 |

(Continued)

OTHER PUBLICATIONS

Swedish Patent Office, Int'l Search Report in PCT/SE2011/050581, Aug. 12, 2011.
Swedish Patent Office, Int'l Prelim. Report on Patentability in PCT/SE2011/050581, Aug. 12, 2012.

*Primary Examiner* — Kevin C Sirmons
*Assistant Examiner* — Deanna K Hall
(74) *Attorney, Agent, or Firm* — Piedmont Intellectual Property

(57) ABSTRACT

Provided is a medicament delivery device (100) that is reliable, safe and intuitive to use and at the same time is easy to use when handling. This is achieved by a medicament delivery device (100) comprising a tubular housing (120, 130) having a proximal end (308) and an opposite distal end (309), an actuator member (110) being coaxially arranged at the distal end (309) of the tubular housing (120, 130) and movably arranged, in relation to the tubular housing (120, 130) and a cap (140) being releasably connected to the proximal end (308) of the tubular housing (120, 130) wherein the medicament device (100) further comprises a longitudinal actuator interlocking member (150) movably arranged within the tubular housing (120, 130) and interactively connected to both the actuator member (110) and to the cap (140) for controlling movement of the actuator member (110). Thus the cap (140) acts as a device enabler, i.e. it is impossible to actuate the medicament delivery device (100) until the cap (140) has been removed.

11 Claims, 12 Drawing Sheets

(51) Int. Cl.
*A61M 5/315* (2006.01)
*A61M 5/20* (2006.01)
*A61M 5/32* (2006.01)
*A61M 5/24* (2006.01)

(56) References Cited

FOREIGN PATENT DOCUMENTS

WO 2005/070481 A1 8/2005
WO 2007/036676 A1 4/2007

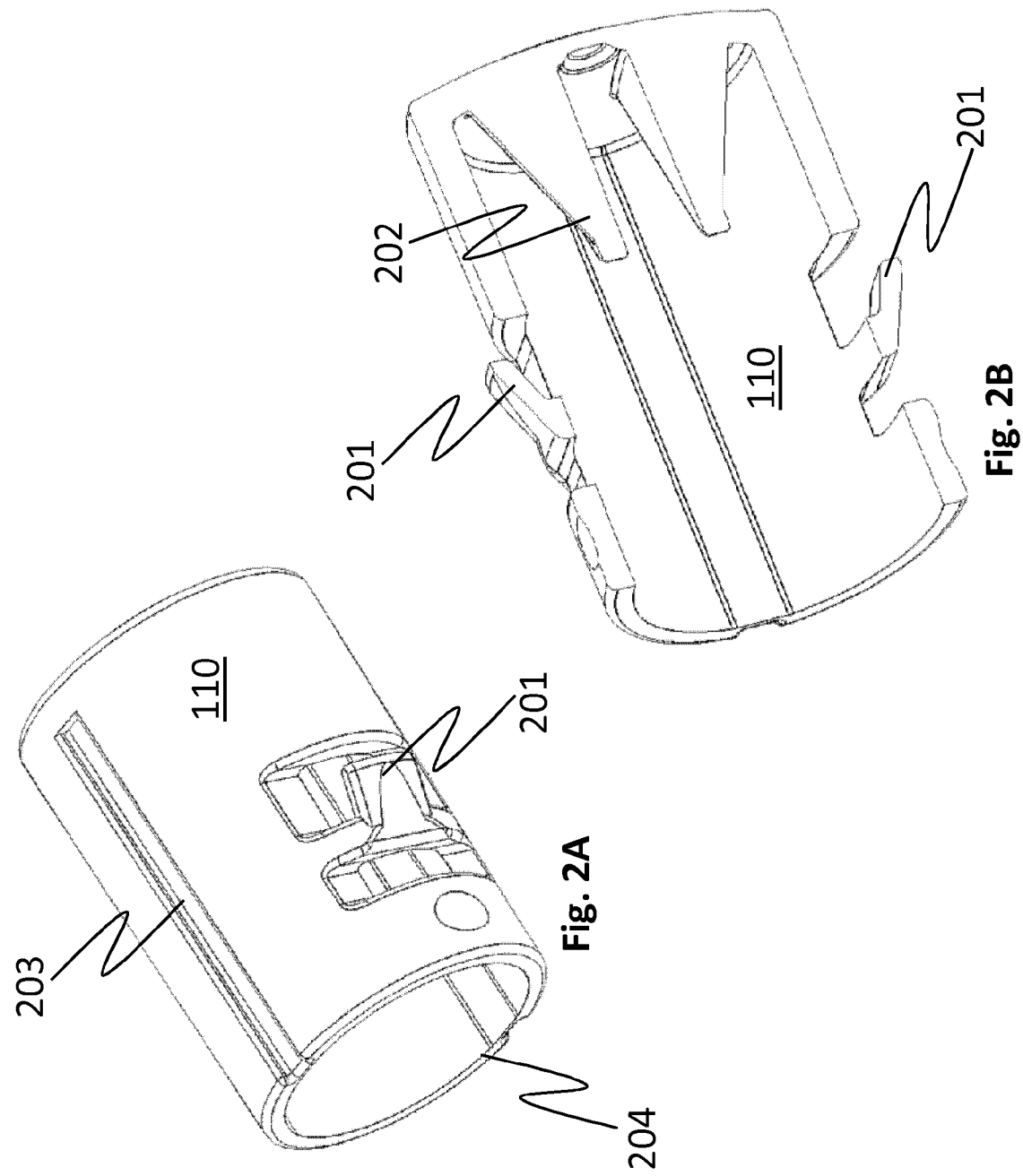

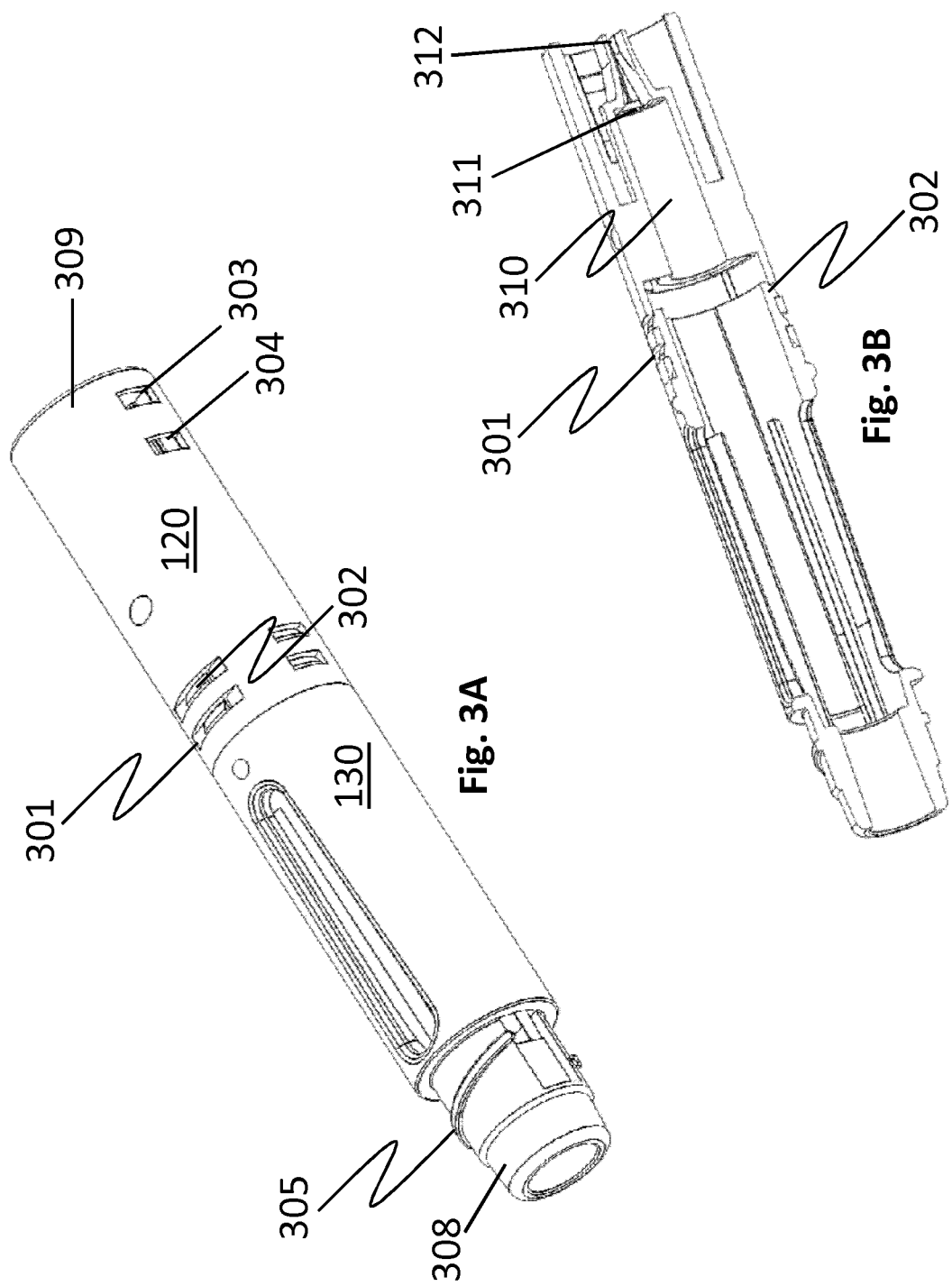

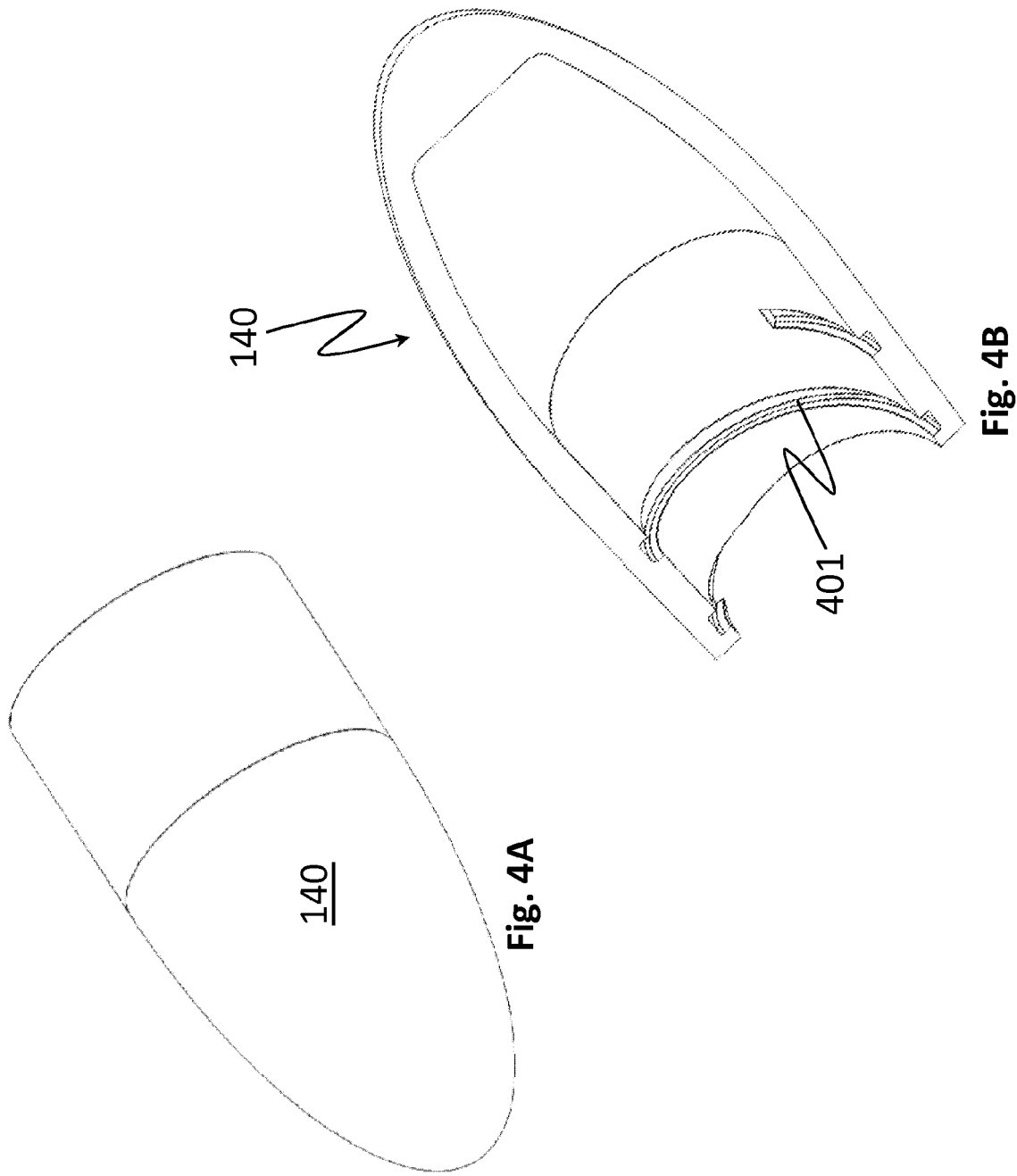

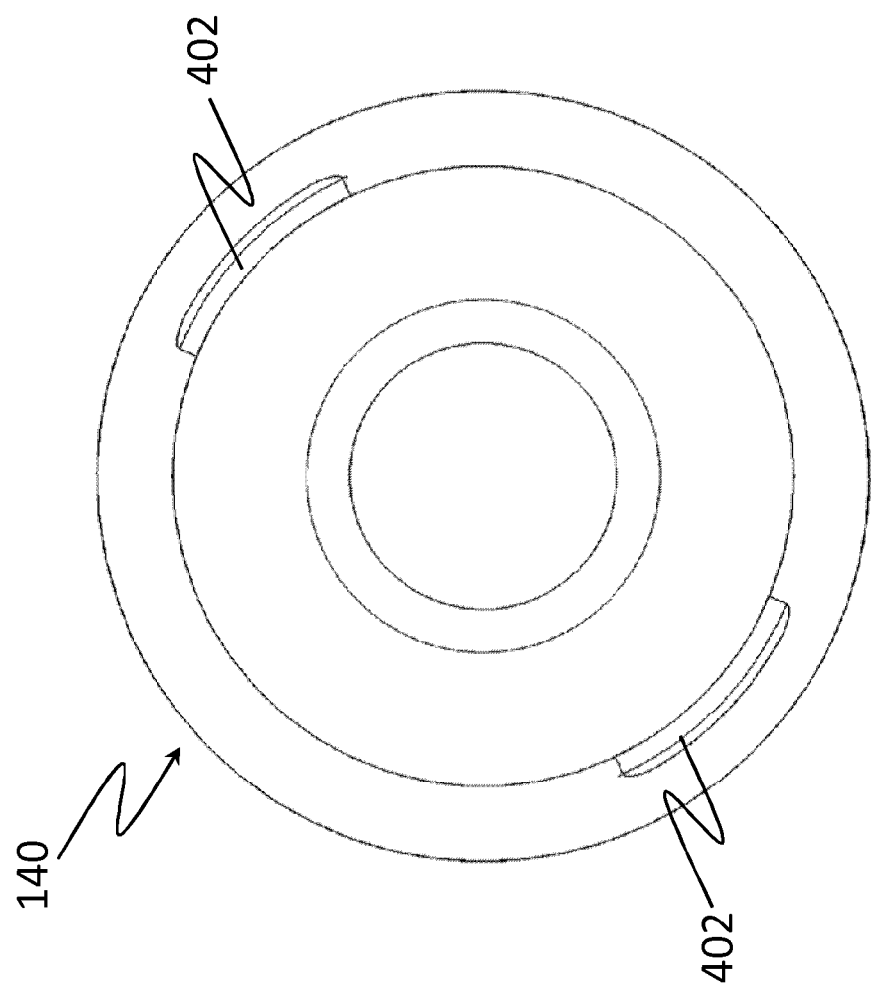

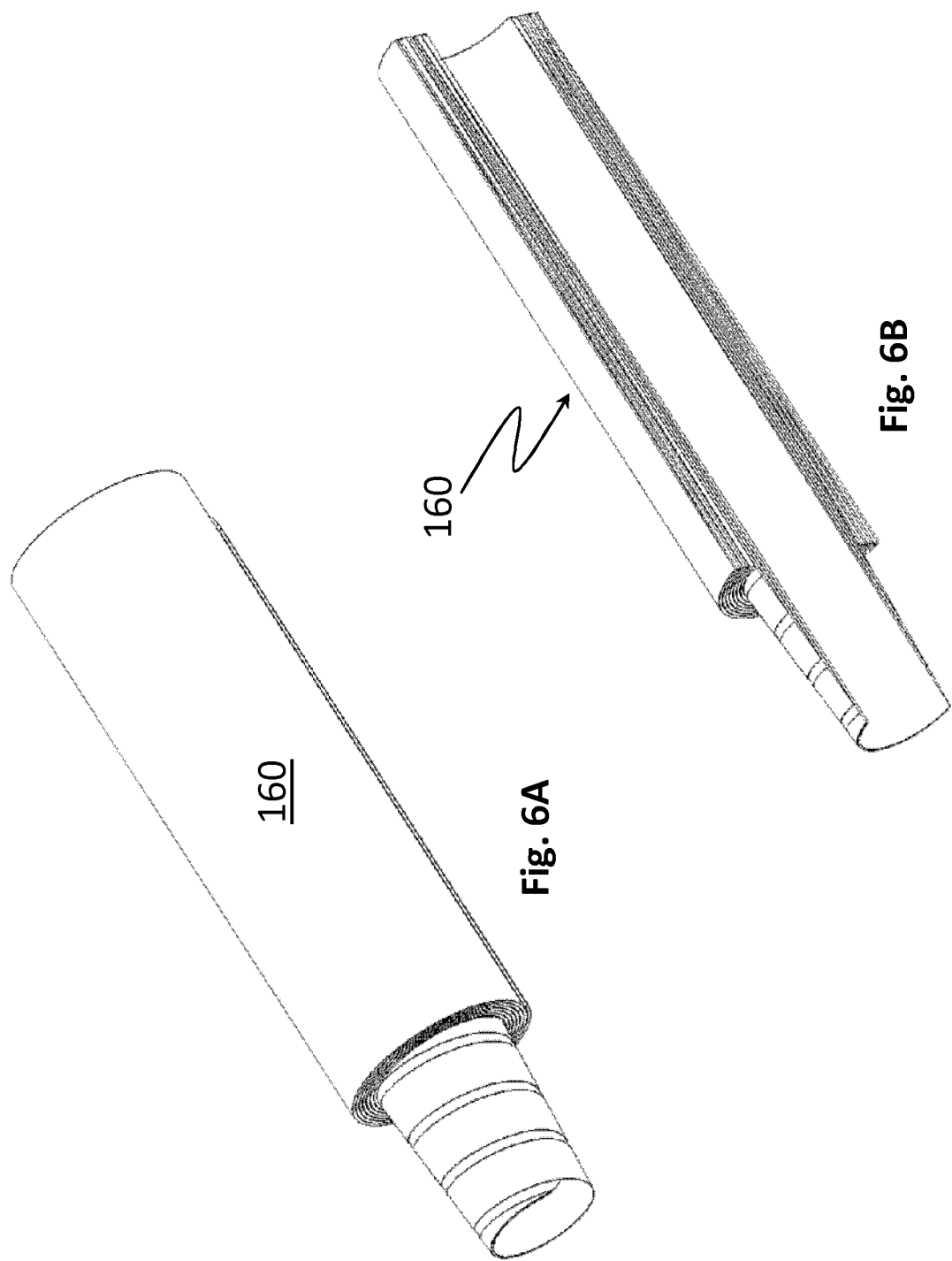

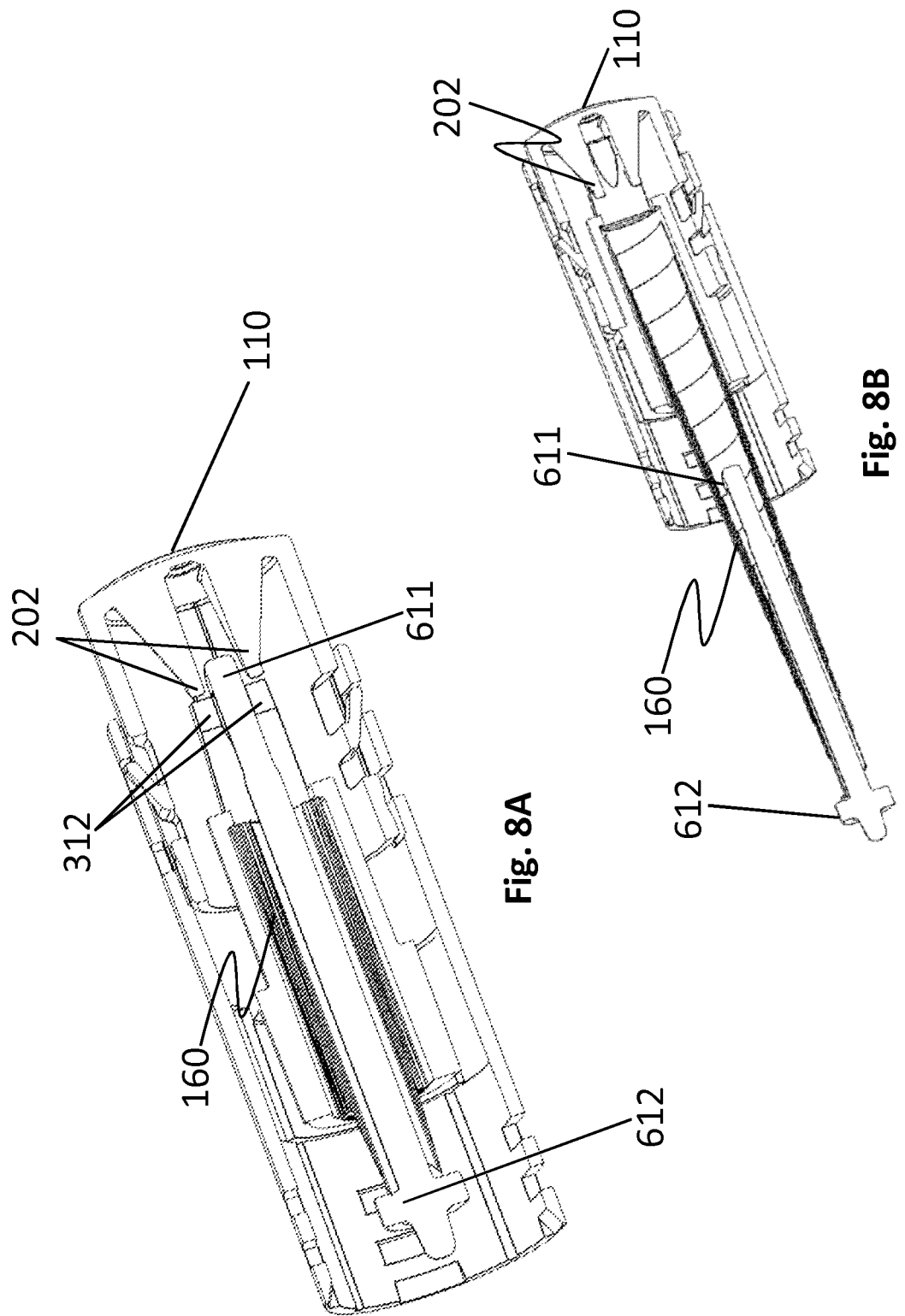

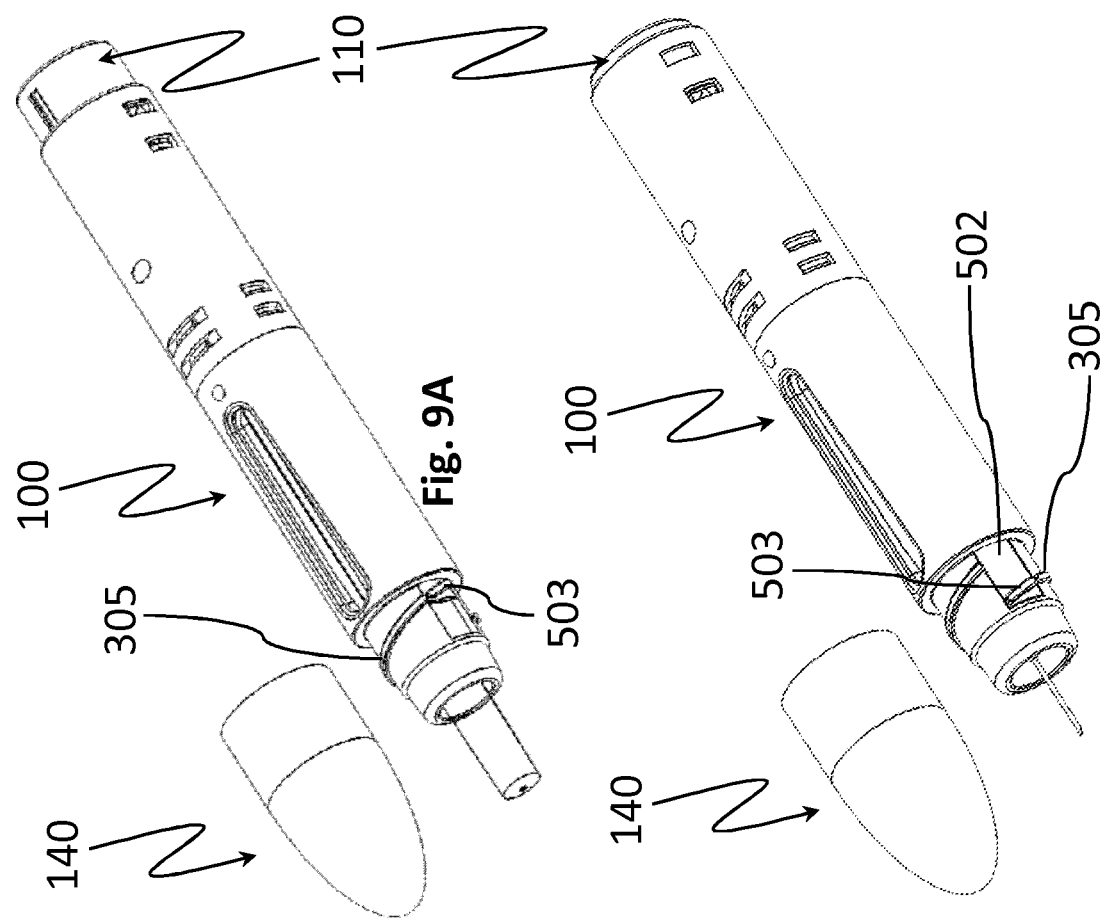

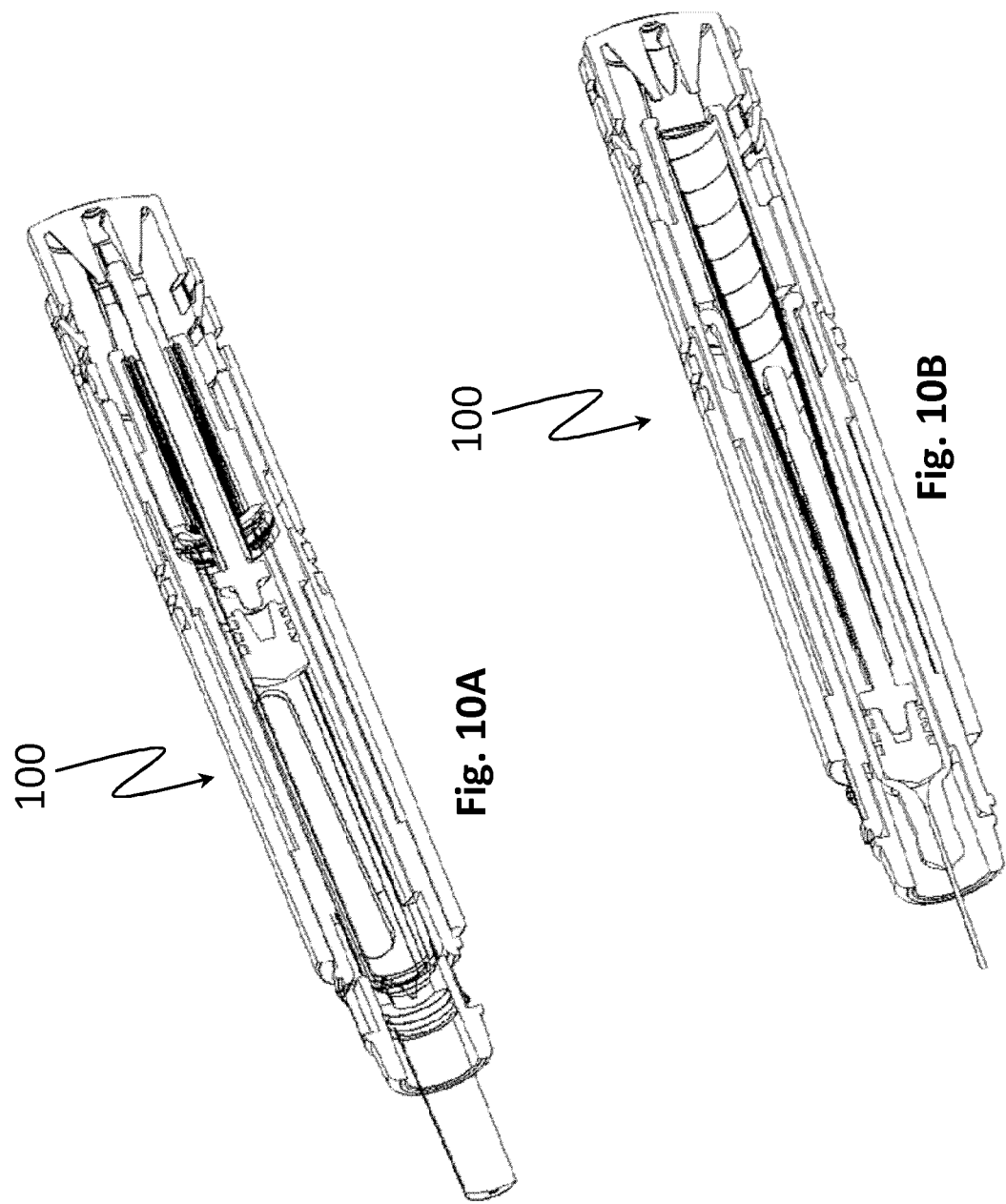

MEDICAMENT DELIVERY DEVICE

TECHNICAL FIELD

The present invention relates to a medicament delivery device for delivering medicament and in particular to a medicament delivery device where safety and handling aspects have been improved by a cap-actuator interlocking arrangement.

BACKGROUND

Basically a medicament delivery device is a device that is simple to use without the need of performing many steps when an individual has to administer a dose of medicament by himself/herself. This requires a solution where the medicament delivery device can be kept as pre-assembled and ready as possible, in order to deliver the medicament in a measured dose, with the minimal number of further manual operations or actions. Thus, to minimize the number of steps needed, in order to perform a medicament delivery, some known prior art devices only need to be actuated against the delivery area, without the need of manual actuation, by pressing a button or the like, which causes the medicament delivery device to perform the delivery. There is however a common need for a medicament delivery device which is very easy to use and which can reliably deliver a set dose of a medicament, in order that the device may be used for self-delivery or by other un-skilled personnel. For example, a person susceptible to anaphylactic shock will normally carry an auto-injector device, pre-charged with adrenalin, to allow an emergency injection of that drug in the event that the patient is suffering from anaphylactic shock. In such conditions, speed is of essence and it may be necessary for a completely un-skilled person to use the injection device to administer the injection. Thus an injection delivery procedure which is easily facilitated and intuitive is highly required.

In U.S. Pat. No. 6,893,420 is disclosed a device arranged with a locking means for locking a latch that prevents the automatic penetration and injection means from being released before mixing of the medicament is finished. Thereby the device of U.S. Pat. No. 6,893,420 provides a pre-assembled medicament delivery device that has great storage facilities and at the same time is easy to use. However, a disadvantage of this prior art solution is that it sometimes is unreliable and may unintentionally be actuated, either by mishap' or by improper usage. One important safety aspect when handling a medicament delivery device is the locking of the injection actuator, before the medicament delivery device is ready for use.

One such device is disclosed in U.S. Pat. No. 6,210,369 describing an injector device having features that prevents unintentional operation of the injector. The penetration and injection is performed manually, by pressing an actuator i.e. a button, thereby enabling the needle to penetrate the injection site. When the injection has been performed the injector is withdrawn, whereby a needle shield extends in a locked position surrounding the needle. As will be noted, a disadvantage with this solution is the extra operation needed to perform an injection. This makes the operation of the device less intuitive; the user needs to find out how to remove a cover over the button, in order to activate the automatic medicament delivery device. This may cause unnecessary delays, which could be harmful or even critical for a patient to be treated.

There is therefore a need for an arrangement that can provide both improved safety handling as well as improved medicament handling. I.e. there is a need for an arrangement where a manually activation for triggering a medicament delivery cannot be performed until a protective cap covering a delivery member is removed. Thus, as can be noted, human handling aspects of the medicament delivery device are crucial and there are several rationales for improving existing solutions.

SUMMARY

An object of the embodiments of the present invention is to provide a medicament delivery device that is reliable, safe and easy and intuitive to use. This is achieved by a medicament delivery device that comprises a tubular housing having a proximal and an opposite distal end; an actuator member which is movable in relation to said tubular housing for triggering a medicament delivery; a medicament container arranged within the tubular housing and having a delivery member protruding through the proximal end of the tubular housing; a cap releasably connected to the proximal end of the tubular housing and covering the delivery member; and interlocking means arranged to interact with both the actuator member and the cap such that the actuator member can only be manually actuated when the cap is removed.

According to a further aspect of the invention, the interlocking means is a longitudinal actuator interlocking member, movably arranged within the tubular housing and arranged to interactively co-act with both the actuator member and the cap so as to avoid unintentional actuation of the actuator member.

According to another aspect of the invention, the actuator interlocking member and the cap are connectable to each other by a first co-acting means and the actuator interlocking member and the actuator member are connectable to each other by a second co-acting means.

According to yet another aspect of the invention, the longitudinal actuator interlocking member is an, axially slidable, member arranged within the tubular housing between a locked position in which the proximal first co-acting means are connected to the corresponding first co-acting means of the cap and the distal second co-acting means are abutting to a corresponding second co-acting means of the actuator member such that the actuator member is prevented from being actuated, and an unlocked position in which the proximal first co-acting means are disconnected from the corresponding first co-acting means of the cap and the distal second co-acting means are abutting to a corresponding second co-acting means of the actuator member such that the actuator member is allowed to be actuated.

According to a further aspect of the invention, the first co-acting means of the interlocking member comprises a partial outer thread, corresponding to an outer thread of the tubular housing both when the interlocking member is in the locked position and in the unlocked position and wherein the corresponding first co-acting means of the cap comprises an inner thread.

According to yet a further aspect of the invention, said tubular housing is arranged to accommodate a medicament container having a delivery member or means for connecting a delivery member to the container.

According to another aspect of the invention, the medicament delivery device further comprises drive means arranged within said tubular housing and adapted to, upon activation, act on a slidable stopper inside the medicament container to expel a dose of medicament; and hold-release means interactively connected to the drive means to hold said drive means in a pre-loaded state, as well as to the actuator member for releasing the drive means from the pre-loaded state, such that when the cap is removed from the tubular housing, the actuator member may be enabled to act on the hold-release means and thereby release the drive means from the pre-loaded state.

According to yet another aspect of the invention, the drive means comprises a plunger rod and an energy accumulating means interactively connected to each other.

According to a further aspect of the invention, the hold-release means comprises flexible a co-acting means arranged on the actuator member, and flexible coupling means arranged on the tubular housing, whereby said flexible co-acting means and said flexible coupling means are arranged to interact with each other to release the drive means from the pre-loaded state.

According to yet a further aspect of the invention, the energy accumulating means is a volute spring or a spiral compression spring or a torsion spring.

According to another aspect of the invention, the actuator member is axially slidable and coaxially arranged within a distal end portion of the tubular housing.

According to another aspect of the invention, the medicament delivery device is a medicament injector and the delivery member is a needle.

By the disclosed medicament delivery device, comprising an actuator interlocking member, unintentional actuation of the medicament delivery device is avoided before the cap is removed and at the same time, a reliable and intuitive medicament delivery device is disclosed. The above described advantages are possible due to the fact that it is impossible to actuate an injection of the medicament contained within the medicament delivery device, without first enabling the medicament delivery device by removing the cap. These and other aspects and advantages of the present invention will become apparent from the following detailed description and from the accompanying drawings.

BRIEF DESCRIPTION OF THE DRAWINGS

In the following description of embodiments of the invention, reference will be made to the accompanying drawings of which:

FIG. 2A shows a perspective detail view of the actuator member.

FIG. 2B illustrates, in perspective, a cross-sectional side view of the actuator member in a more detailed view.

FIG. 3A illustrates a perspective view of the tubular housing

FIG. 3B illustrates, in perspective, a cross-sectional side view of the tubular housing FIG. 4A shows a perspective view of an exemplary cap FIG. 4B illustrates, in perspective, a cross-sectional side view of the cap FIG. 4C illustrates a distal view of the cap -FIG. 6B illustrates a perspective view and a cross-sectional side view of the resilient member.

FIG. 8A illustrates in perspective, the distal part of the tubular housing in a first inactivated position.

FIG. 8B illustrates in perspective, the distal part of the tubular housing in a second activated position.

FIG. 9A illustrates, in perspective, an exemplary medicament delivery device in a pre-loaded state, i.e. a first inactivated position.

FIG. 9B illustrates, in perspective, an exemplary medicament delivery device in an actuated state, i.e. a second activated position.

FIG. 10A and FIG. 10B illustrates also perspective views of the operations described in FIG. 9A and FIG. 9B, however in FIG. 10A and FIG. 10B these operations are illustrated in cross-section.

DETAILED DESCRIPTION

Embodiments of present invention will now be described in detail. As it should be noted in present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

According to the main aspect of the invention, a medicament delivery device comprises a tubular housing having a proximal and an opposite distal end; an actuator member movably arranged in relation to said tubular housing for triggering a medicament delivery; a medicament container arranged within the tubular housing and having a delivery member protruding through the proximal end of the tubular housing; a cap releasably connected to the proximal end of the tubular housing and covering the delivery member; and interlocking means arranged to interact with both the actuator member and the cap such that the actuator member can only be manually actuated when the cap is removed.

According to a further aspect of the invention, the interlocking means is a longitudinal actuator interlocking member, movably arranged within the tubular housing and arranged to interactively co-act with both the actuator member and the cap for avoiding unintentional actuation of the actuator member.

According to another aspect of the invention, the actuator interlocking member and the cap are connectable to each other by a first co-acting means and wherein the actuator interlocking member and the actuator member are connectable to each other by a second co-acting means.

Figure 1:
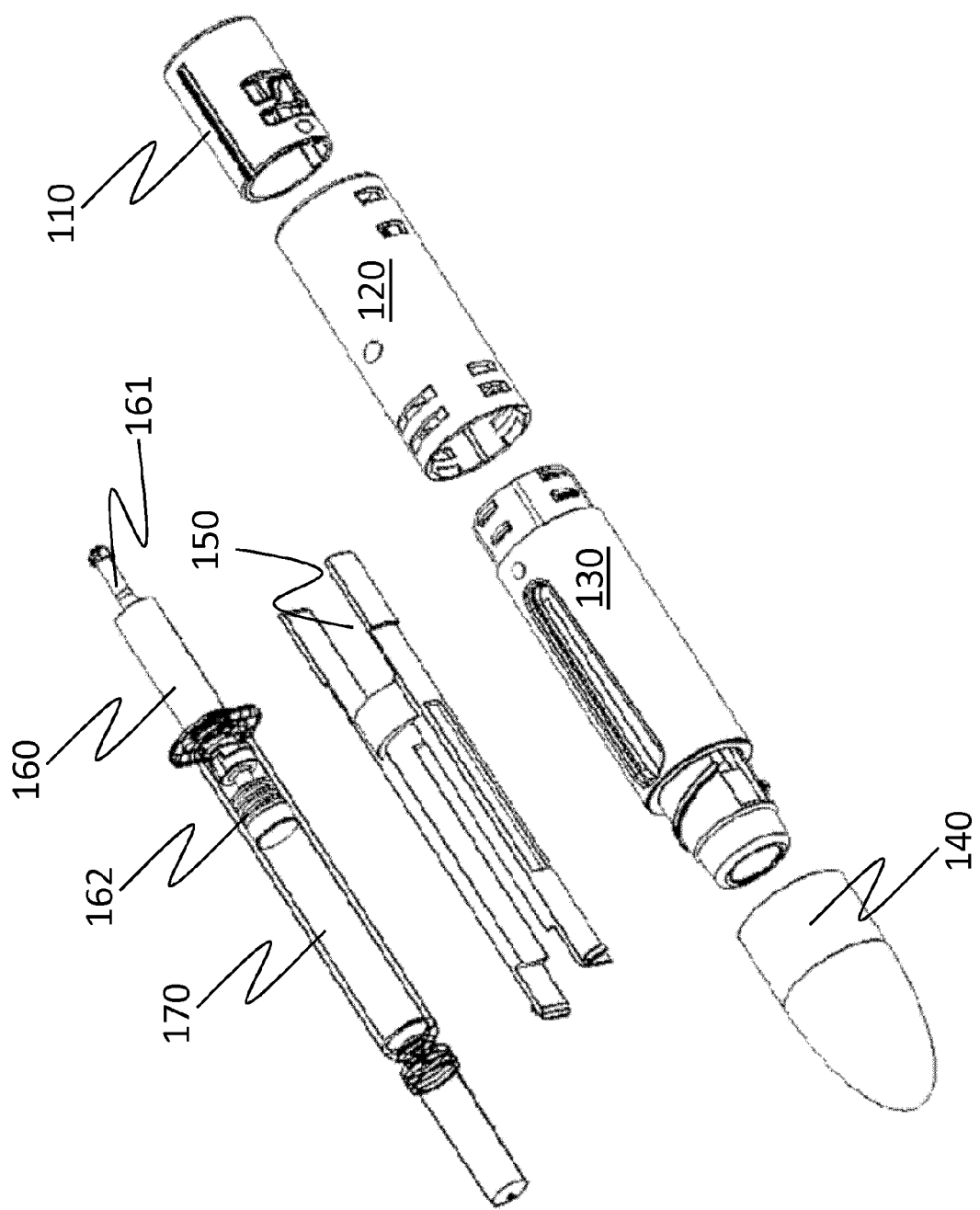
FIG. 1 is a perspective view of exemplary components of a complete medicament delivery device according to the invention.

An exemplary embodiment of the present invention is shown in the FIGS. 1-10. The exemplary embodiment shown in the figures is a medicament injector but is not restricted to it. FIG. 1 is a perspective view of exemplary components of a complete medicament delivery device 100 according to the invention. In FIG. 1 is illustrated the pre-assembled medicament delivery device 100 having the cap 140 interactively mounted to the tubular housing 120, 130 and the medicament container 170, arranged within the tubular housing and having the delivery member as e.g. a needle, a nozzle, a mouth piece or the like protruding through the proximal end of the tubular housing. The cap is arranged to cover the delivery member when the cap is connected to the proximal end 308 of the tubular housing 120,130. In the exemplary embodiment of the invention, the tubular actuator member 110 is axially slidable and coaxially arranged within a distal end 309 portion of the tubular housing 120,130, but not restricted to it.

The medicament delivery device 100 further comprises drive means arranged within said tubular housing adapted to, upon activation, act on a slidable stopper 162 inside the medicament container 170 to expel a dose of medicament; and hold-release means interactively connected to the drive means to hold said drive means in a pre-loaded state, as well as to the actuator member 110 to release the drive means form the pre-loaded state, such that when the cap 140 is removed from the tubular housing, the actuator member may be enabled to act with the hold-release means and thereby release the drive means from the pre-loaded state. The drive means comprises a plunger rod 161 and an energy accumulating means 160 interactively connected to each other.

Figure 6C:
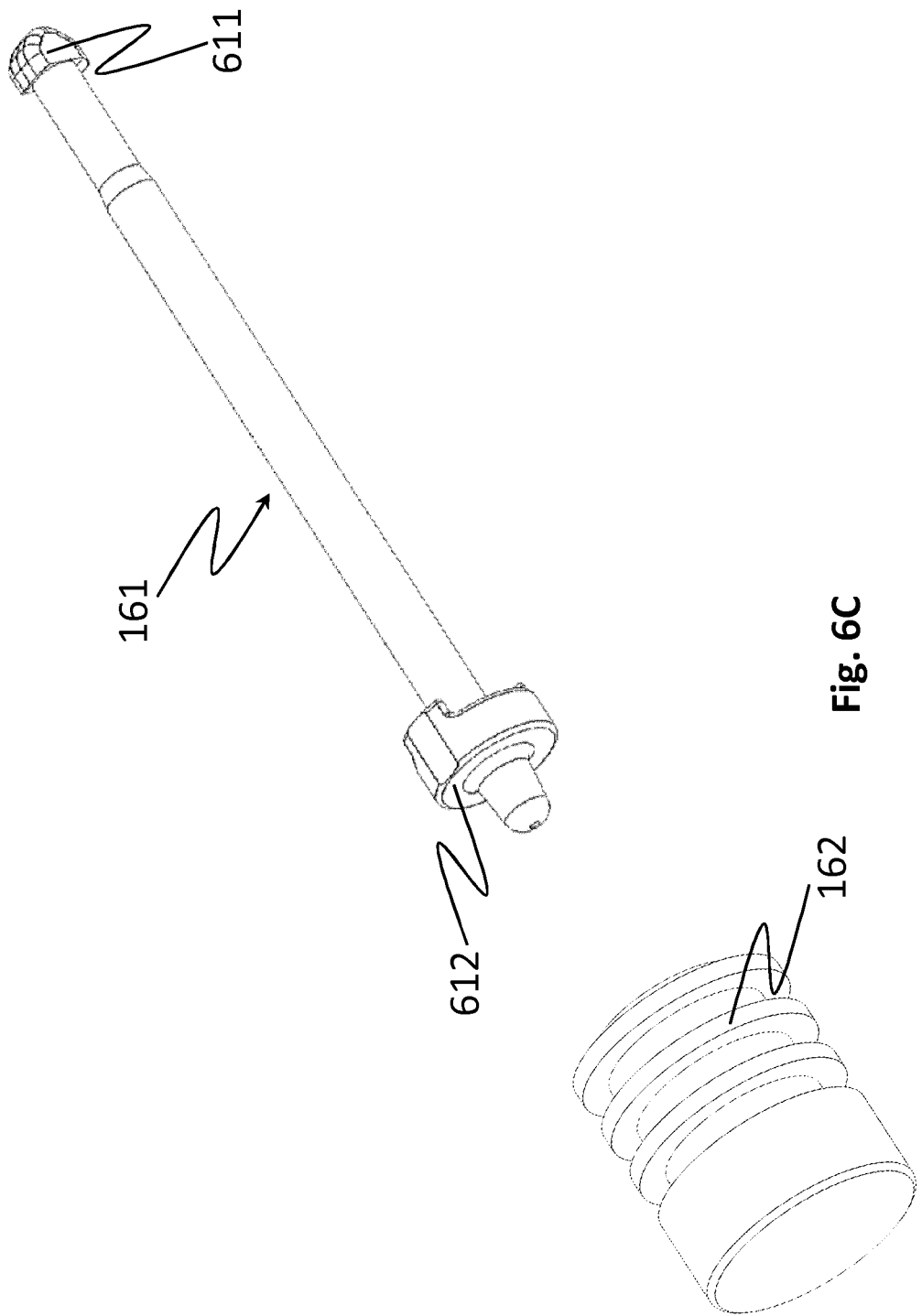
FIG. 6C illustrates a perspective view of the plunger rod.

In the exemplary embodiment of the invention, as shown in FIG. 6C, the plunger rod 161 comprises a plunger rod head 612 for pushing the slidable stopper 162 and a plunger rod coupling member 611. The tubular housing 120,130 comprises cut-outs 303,304, FIG. 3A, adapted to receive a third co-acting means 201, FIG. 2B, of the actuator member 110, for interactively and fixedly attaching the actuator member 110 to the tubular housing 120,130. In an exemplary embodiment of the invention the further cut-out 303,304 comprises two openings adapted to receive the third co-acting means 201 of the actuator member 110 in two steps, a first cut-out 303 for releaseably attaching the actuator member 110 to the tubular housing 120,130 in a first inactivated position, and a second cut-out 304, whereby the actuator member 110 is fixedly attached to the tubular housing 120,130 in a second activated position after the actuator member has been moved towards the proximal end. The actuator member 110 also comprises guiding means 203 arranged to interact with corresponding guiding means on the inner surface of the tubular housing, which in the exemplary embodiment of the invention are groove tracks; and the corresponding guiding means of the tubular member are longitudinally extending ledges which guide the axial movement of the actuator member 110 within the tubular housing 120,130.

The hold-release means comprises flexible co-acting means 202 arranged on the actuator member, and flexible coupling means 312 arranged to the tubular housing, whereby said flexible co-acting means 202 and said flexible coupling means 312 are arranged to interact with each other to release the drive means from the pre-loaded state. In the exemplary embodiment of the invention, the flexible co-acting means 202 are two flexible tongues, FIG. 2B, extending in a proximal direction from the actuator member, and the flexible coupling means 312 are two flexible tongues extending in a distal direction from an inner distal end transversal wall 311 of the tubular housing, FIG. 3B, whereby said flexible co-acting means 202 and said flexible coupling means 312 are arranged to interact with each other as will be explained below.

FIG. 3A illustrates a perspective view of the tubular housing 120, 130. A distal part 120 of the tubular housing 120,130 comprises a recess, an opening or a cut-out 301 adapted to receive a corresponding fastening means 302 of a proximal part 130 of the tubular housing 120,130 for fixedly attaching the distal part 120 to the proximal part 130 of the tubular housing 120,130 during the manufacturing process of the medicament delivery device 100. In an exemplary embodiment of the invention, the corresponding fastening means 302 of the proximal part 130 of the tubular housing 120,130 comprises two radial outward extending flexible tongues which are adapted to lock into the cut-out 301 which is adapted to receive said corresponding fastening means 302. The proximal part 130 of the tubular housing 120,130 also comprises a coupling means 305 in the shape of radial outward extensions, i.e. an outward extending thread, adapted to interact and engage with a corresponding coupling means 401, i.e. an inner thread, of the cap 140. The proximal part 130 of the tubular housing 120,130 further comprises a recess, or a track groove, adapted to guide the actuator interlocking member 150.

FIG. 3B illustrates, in a perspective cross-sectional view of the tubular housing 120, 130. The distal end 309 part of the tubular housing 120,130 comprises a housing compartment 310 for housing the energy accumulating means 160. In the most distal part of the tubular housing 120,130 is situated the coupling means 312 for interactively coupling the plunger rod 161 to the tubular housing 120,130.

FIG. 4A shows a perspective view of an exemplary cap 140 and FIG. 4B illustrates a perspective, exploded view of the cap 140 comprising a coupling means 401, e.g. in the form of threads on an inner surface of the cap 140, adapted to be interactively connected to a corresponding coupling means 305 of the tubular housing 120,130.

FIG. 4C illustrates a distal view of the cap 140, showing a longitudinal recess 402 adapted to receive and contain a proximal portion of the actuator interlocking member 150. The cap 140 also comprises the coupling means 401, e.g. in the shape of internal threads, interactively connected to corresponding coupling means 305 of the tubular housing 120, 130. Preferably, the pitches of the threads are chosen such that there is a major longitudinal movement of the cap 140 in the proximal direction for a small turning angle, in order to avoid the user needing to turn the cap 140 more than about half a turn when performing the operation, so as to avoid them having to change grip to finish the operation of removing the cap 140.

Figure 5:
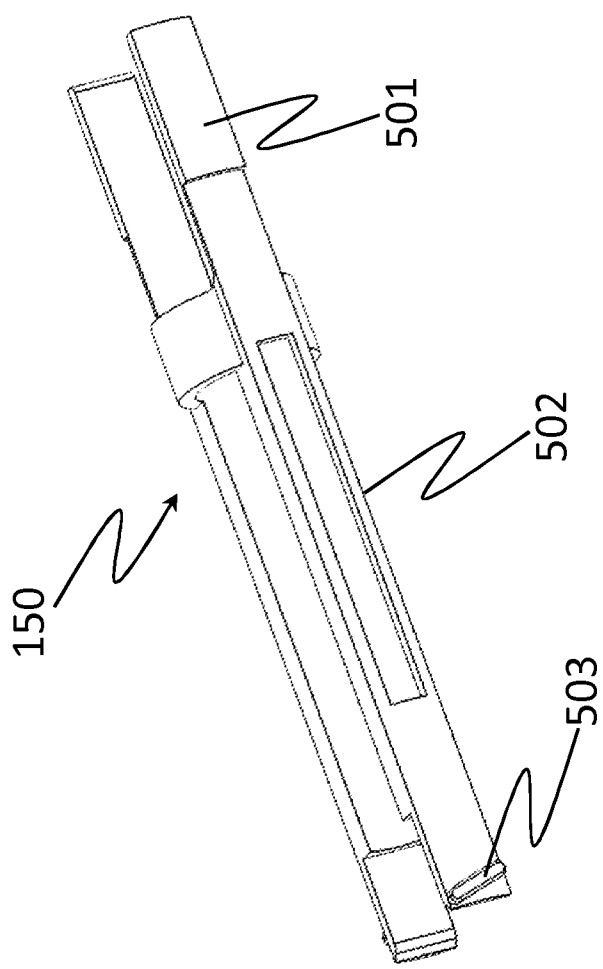
FIG. 5 is a perspective view of the actuator interlocking member FIG. 6A

In the exemplary embodiment, the second co-acting means comprises a proximal annular ledge 204, FIG. 2A, of the actuator member 110 and at least one distally extending tongue 501, FIG. 5, of the actuator interlocking member 150. Also the first co-acting means comprises a partial outer thread 503 on the outer proximal end surface of at least one proximally extending tongue 502 of the actuator interlocking member 150, FIG. 5, and the coupling means 401, e.g. in the shape of internal threads, on the inner circumferential surface of the cap 140. In the exemplary embodiment of the invention the partial outer thread 503 has the same thread pitch as the threads of the outer thread of the tubular housing 120,130; i.e. the co-acting means 305 of the tubular housing 120,130.

FIG. 6A illustrates a cross-sectional side view of the energy accumulating means 160 and FIG. 6B illustrates the same energy accumulating means 160 but now in a cross-sectional side view. In the exemplary embodiment, the energy accumulating means is a volute spring but a spiral compression spring or a torsion spring can be used as well.

FIG. 6C illustrates a perspective side view of the plunger rod 161 and the slidable stopper 162. The plunger rod comprises the plunger rod coupling member 611, and the plunger rod head 612.

Figure 7:
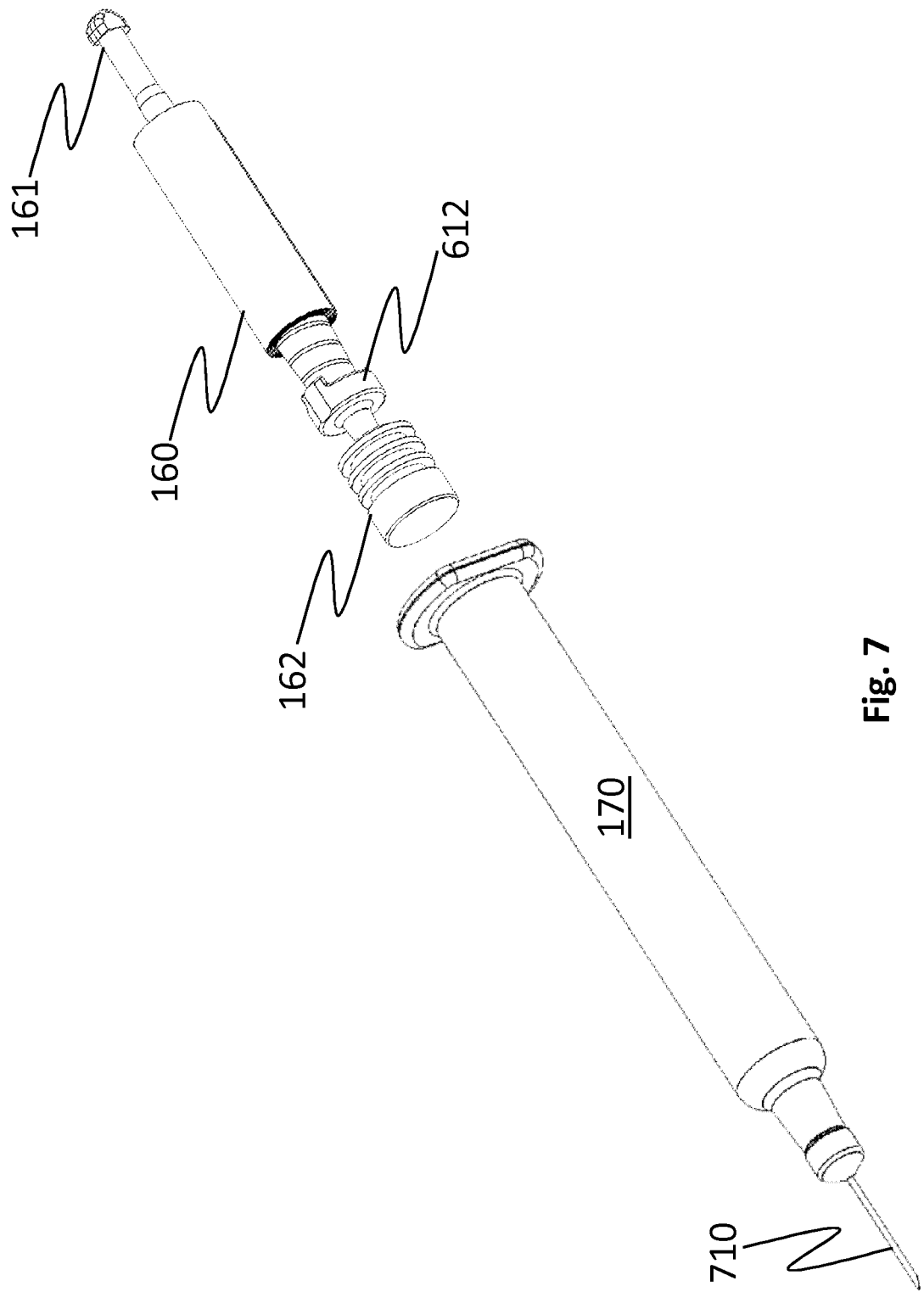
FIG. 7 illustrates illustrates a perspective view of the drive means and the container.

FIG. 7 illustrates the interior components of the medicament delivery device 100 including the plunger rod 161 having the plunger rod head 612, the energy accumulating member 160, the slidable stopper 162, the medicament container 170 and the delivery member as e.g. a needle 710.

FIG. 8A illustrates a cross-sectional perspective view, of the distal part of the tubular housing 120,130 and of the actuator member 110 in the first inactivated position wherein the plunger rod 161 and the energy accumulating means 160 are in a pre-loaded state i.e. the plunger rod coupling member 611 is releasably connected to the flexible coupling means 312 and a distal end of the energy accumulating means 160 is pre-loaded and arranged between the proximal annular surface of the inner distal end wall 311 of the tubular housing 120,130 and the annular distal surface of the plunger rod head 612

FIG. 8B illustrates in a cross-sectional perspective view, of the distal part of the tubular housing 120,130 and of the actuator member 110 in the second activated position wherein the actuator 110 has been pressed down in a proximal direction, thus forcing the flexible co-acting means 202 in a proximal direction to enable the flexible coupling means 312 to expand in a radial outward direction and thereby allow the plunger rod coupling member 611 to be released from said flexible coupling means 312.

FIG. 9A illustrates, in perspective, an exemplary medicament delivery device 100 having the actuator member 110 in the first inactivated position, coaxially arranged at the distal end 309 of the tubular housing 120,130 and the cap 140 releasably connected, i.e. detachable, to the proximal end 308 of the tubular housing 120,130. In the exemplary embodiment, the longitudinal actuator interlocking member 150 is axially slidable within the tubular housing between a locked position in which the proximal first co-acting means 503 are connected to the corresponding first co-acting means 401 of the cap 140 and the distal second co-acting means 501 are abutting to the corresponding second co-acting means 204 of the actuator member 110 such that the actuator member is prevented from being actuated, and an unlocked position in which the proximal first co-acting means 503 are disconnected from the corresponding first co-acting means 401 of the cap 140 and the distal second co-acting means 501 are abutting to a corresponding second co-acting means 204 of the actuator member 110 such that the actuator member is allowed to be actuated.

FIG. 9B illustrates, in perspective, an exemplary medicament delivery device 100 wherein the actuator member 110 is in the second activated position and wherein the longitudinal actuator interlocking member 150 has been moved from the locked position to the unlocked position. Further, the first co-acting means 503 of the interlocking member 150 which in the exemplary embodiment is illustrated as a partial outer thread, corresponds to the outer thread 305 of the tubular housing both when the interlocking member is in the locked position and in the unlocked position.

FIG. 10A and FIG. 10B illustrate also a perspective cross-sectional view of the operations described in FIG. 9A and FIG. 9B The present invention is not limited to the above-described preferred embodiment. Various alternatives, modifications and equivalents may be used. Therefore, the above embodiment should not be taken as limiting the scope of the invention, which is defined by the appended claims.

The invention claimed is:

1. A medicament delivery device, comprising:
a tubular housing having a proximal end and an opposite distal end;
an actuator member movably arranged in relation to the tubular housing for triggering a medicament delivery;
a medicament container arranged within the tubular housing and having a delivery member protruding through the proximal end of the tubular housing;
a cap releasably connected to the proximal end of the tubular housing and covering the delivery member;
an interlocking mechanism configured to interact with the actuator member and the cap such that the actuator member can be manually actuated only when the cap is removed.

2. The medicament delivery device of claim 1, wherein the locking mechanism includes a longitudinal actuator interlocking member movably arranged within the tubular housing and arranged to co-act interactively with the actuator member and the cap.

3. The medicament delivery device of claim 2, wherein the actuator interlocking member and the cap are configured to connect to each other by respective proximal first co-acting devices, and the actuator interlocking member and the actuator member are configured to connect to each other by respective distal second co-acting devices.

4. The medicament delivery device of claim 3, wherein the longitudinal actuator interlocking member includes a member in the tubular housing that is axially slidable between a locked position, in which the first co-acting devices are connected to each other and the second co-acting devices abut each other thereby preventing manual activation of the actuator member, and an unlocked position, in which the first co-acting devices are disconnected from each other and the second co-acting devices abut each other thereby permitting activation of the actuator member.

5. The medicament delivery device of claim 4, wherein the first co-acting device of the interlocking member comprises a partial outer thread that corresponds to an outer thread of the tubular housing when the interlocking member is in the locked position and in the unlocked position, and the first co-acting device of the cap comprises an inner thread.

6. The medicament delivery device of claim 5, further comprising:
a drive mechanism in the tubular housing configured, upon activation, to act on a slidable stopper in the medicament container to expel a dose of medicament; and
a hold-release mechanism interactively connected to the drive mechanism for holding the drive mechanism in a pre-loaded state and to the actuator member for releasing the drive mechanism from the pre-loaded state, such that when the cap is removed from the tubular housing, the actuator member is enabled to act on the hold-release mechanism and thereby release the drive mechanism from the pre-loaded state.

7. The medicament delivery device of claim 6, wherein the drive mechanism comprises a plunger rod and an energy accumulating device interactively connected to each other.

8. The medicament delivery device of claim 7, wherein the hold-release mechanism comprises a flexible co-acting device on the actuator member and a flexible coupling device of the tubular housing, whereby the flexible co-acting device and the flexible coupling device are configured to interact with each other to release the drive mechanism from the pre-loaded state.

9. The medicament delivery device of claim 8, wherein the energy accumulating device is a volute spring or a spiral compression spring or a torsion spring.

10. The medicament delivery device of claim 1, wherein the actuator member is axially slidable and coaxially arranged within a distal end portion of the tubular housing.

11. The medicament delivery device of claim 1, wherein the device is a medicament injector and the delivery member is a needle.

* * * * *